(12) United States Patent
Agbodoe

(10) Patent No.: US 8,657,823 B2
(45) Date of Patent: Feb. 25, 2014

(54) RONGEUR WITH DETACHABLE TIPS

(75) Inventor: Victor B. Agbodoe, Stoughton, MA (US)

(73) Assignee: Specialty Surgical Instrumentation Inc., Antioch, TN (US)

( * ) Notice: Subject to any disclaimer, the term of this patent is extended or adjusted under 35 U.S.C. 154(b) by 162 days.

(21) Appl. No.: 13/316,969

(22) Filed: Dec. 12, 2011

(65) Prior Publication Data
US 2013/0150861 A1    Jun. 13, 2013

(51) Int. Cl.
*A61B 17/16*    (2006.01)

(52) U.S. Cl.
USPC .......................................................... 606/83

(58) Field of Classification Search
USPC .................................................. 606/83, 167
See application file for complete search history.

(56) References Cited

U.S. PATENT DOCUMENTS

| | | | |
|---|---|---|---|
| 4,990,148 A | 2/1991 | Worrick, III et al. | |
| 5,273,519 A | 12/1993 | Koros et al. | |
| 5,323,765 A * | 6/1994 | Brown | 600/104 |
| 5,653,713 A | 8/1997 | Michelson | |
| 5,766,177 A | 6/1998 | Lucas Dean | |
| 6,142,997 A | 11/2000 | Michelson | |
| 6,200,320 B1 | 3/2001 | Michelson | |
| 6,575,977 B1 | 6/2003 | Michelson | |
| 6,695,849 B2 | 2/2004 | Michelson | |
| 6,991,633 B2 | 1/2006 | Agbodoe | |
| 7,011,663 B2 | 3/2006 | Michelson | |
| 7,014,638 B2 | 3/2006 | Michelson | |
| 2004/0044346 A1 * | 3/2004 | Boury | 606/83 |
| 2004/0102783 A1 | 5/2004 | Sutterlin | |
| 2004/0122433 A1 | 6/2004 | Loubens | |
| 2008/0161809 A1 | 7/2008 | Schmitz | |
| 2011/0190773 A1 | 8/2011 | Michelson | |

FOREIGN PATENT DOCUMENTS

| | | | | |
|---|---|---|---|---|
| WO | WO 2007065530 A2 * | 6/2007 | | A61B 17/28 |
| WO | 2009010192 A2 | 1/2009 | | |

OTHER PUBLICATIONS

Translation of WO 2007/065530 to Schilling.*

* cited by examiner

*Primary Examiner* — Christian Sevilla
(74) *Attorney, Agent, or Firm* — Hayes Soloway P.C.

(57) ABSTRACT

A rongeur has an elongated shank having a distal end and a proximal end. An elongated crossbar, which moves between a retracted position and a tissue capturing position position, has a distal end and a proximal end and reciprocates axially with respect to the shank. A first tip is selectively connected to the shank. The first tip has a proximal end and a distal end. The proximal end has a reduced diameter post. In the selectively connected position, the reduced diameter post of the first tip is received in a bore of the shank. A second tip is selectively connected to the crossbar. The second tip has a proximal end and a distal end. The proximal end has a reduced diameter post. In the selectively connected position, the reduced diameter post of the second tip is received in a bore of the crossbar.

15 Claims, 4 Drawing Sheets

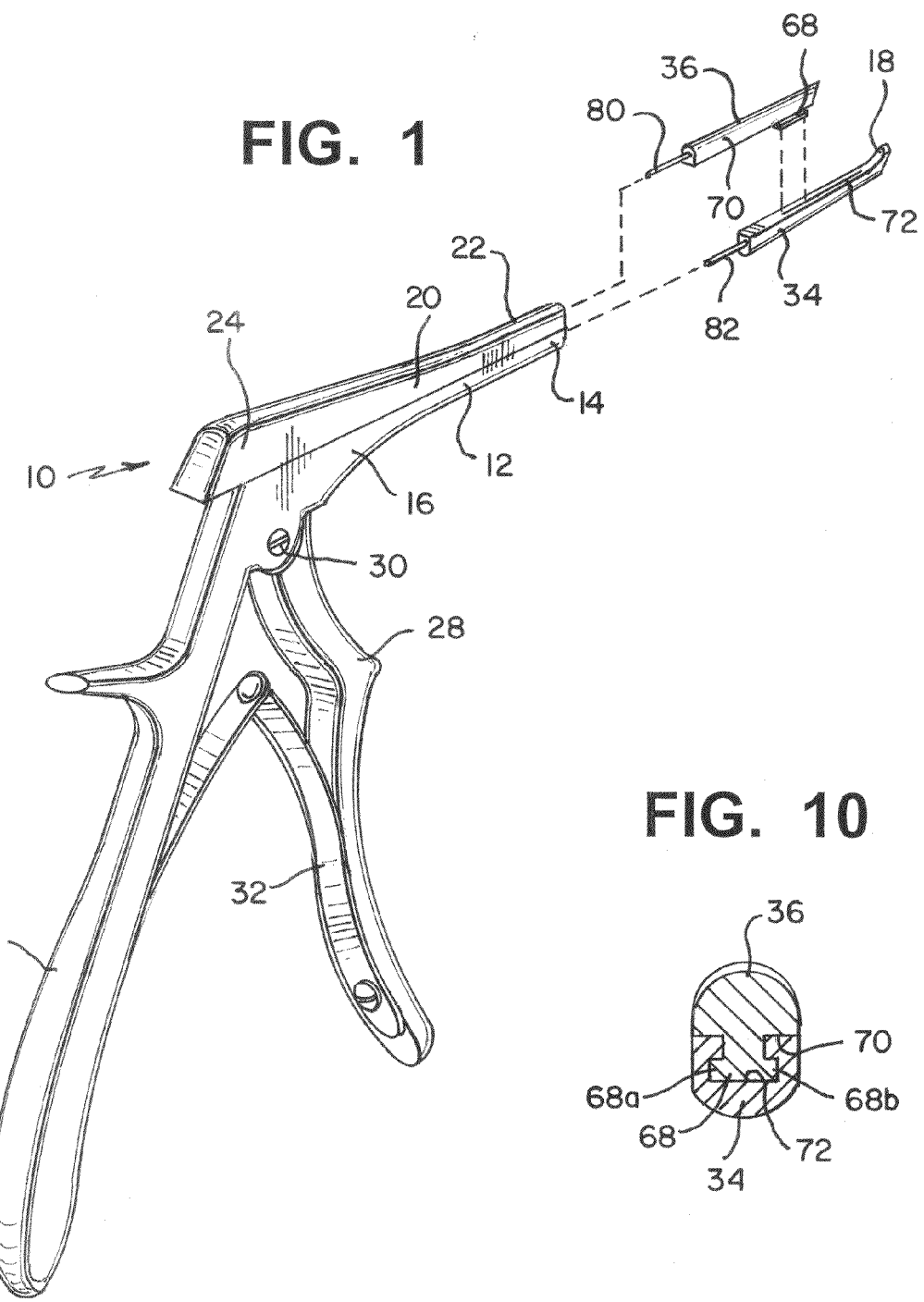

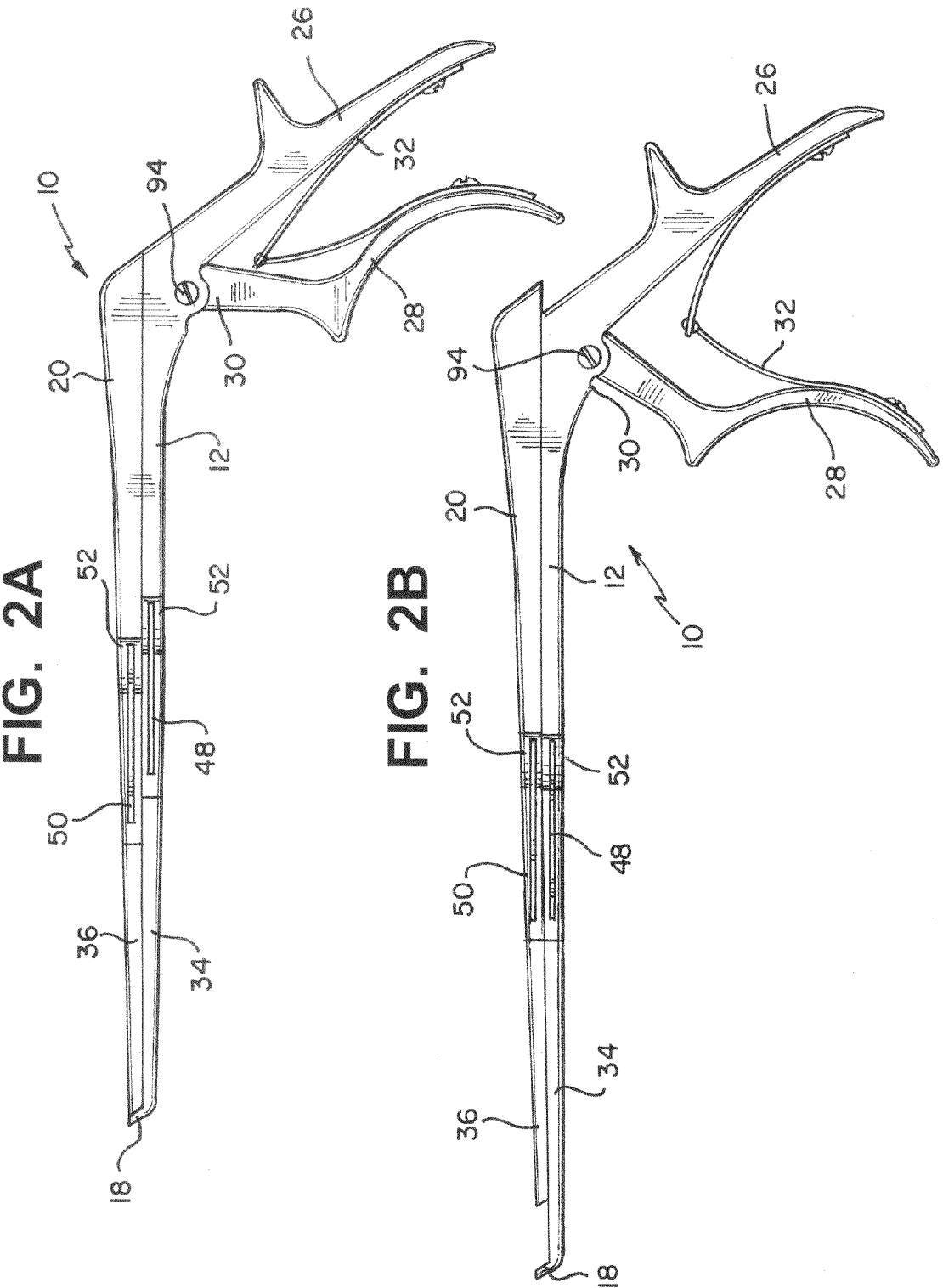

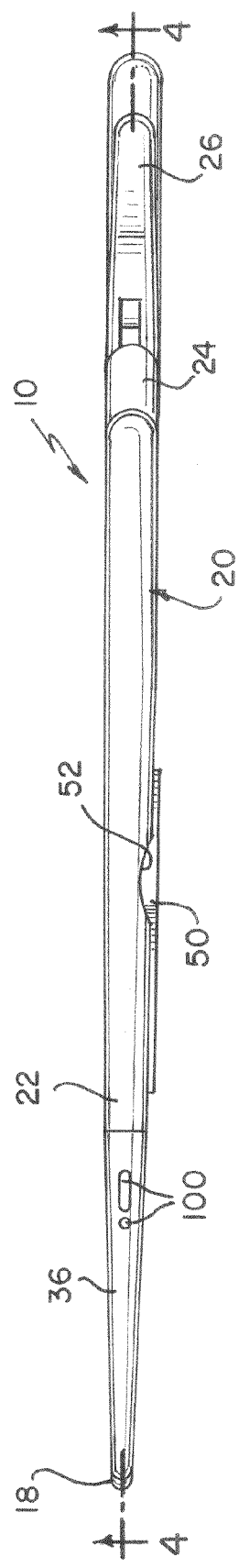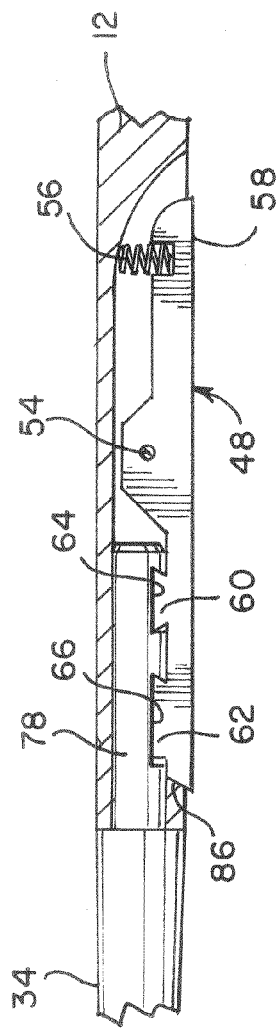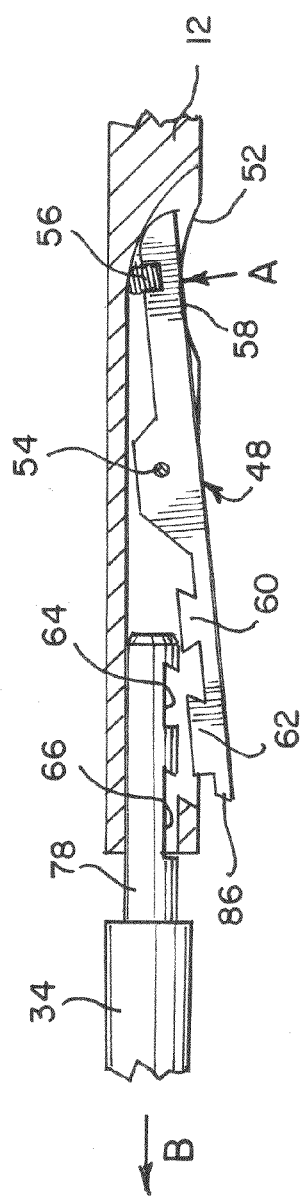

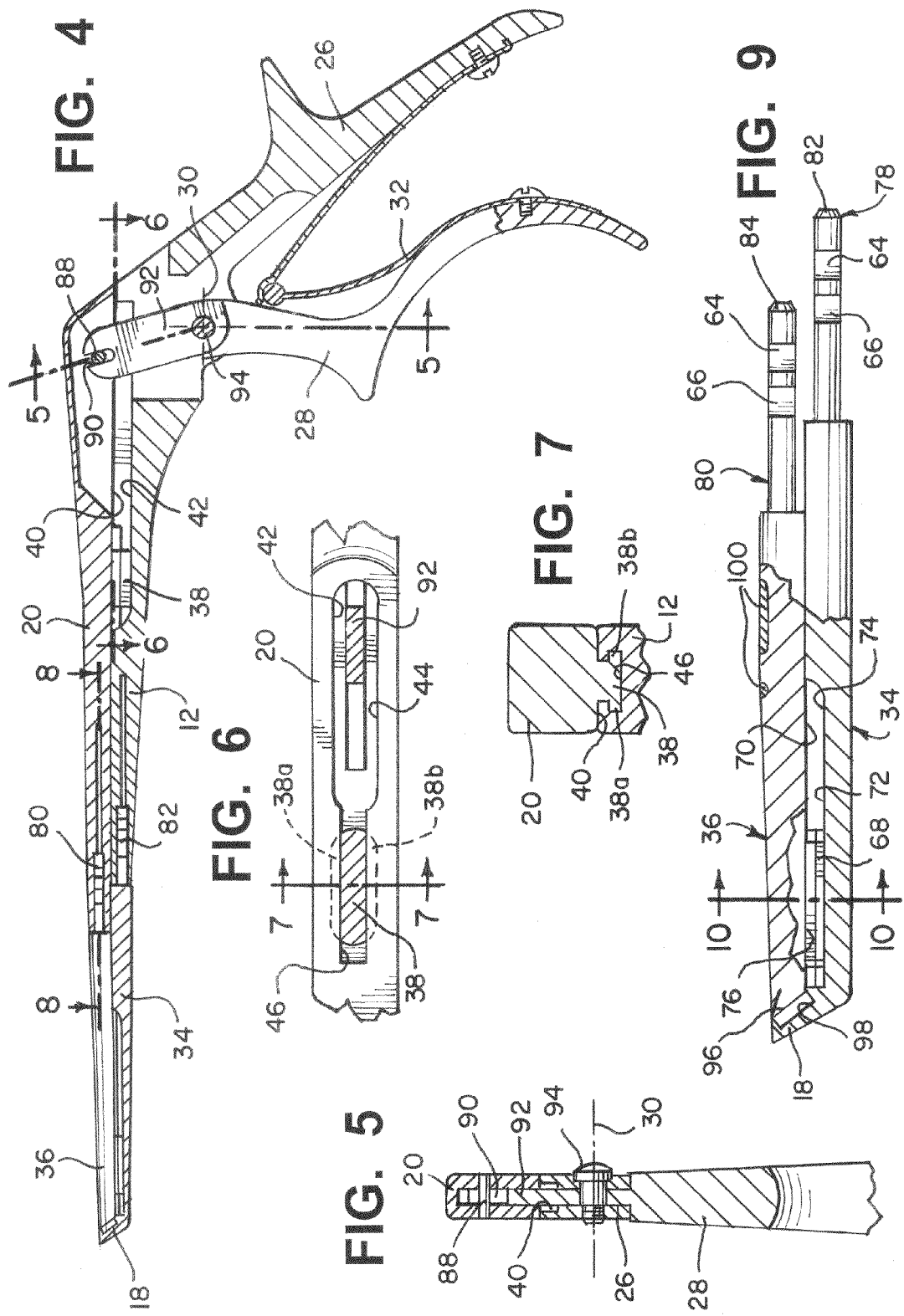

RONGEUR WITH DETACHABLE TIPS

FIELD OF THE INVENTION

The present invention relates to a rongeur, and more particularly to a rongeur having a detachable tip.

BACKGROUND

The rongeur is a medical instrument used for a variety of purposes. It is particularly useful for removing small amounts of bone, cartilage or other body material from inside small spaces of the knee or between vertebrae. A rongeur usually includes a long fixed shank with an anvil or footplate at its distal end and a handle at its proximal end. A cross bar slideably engages the shank and reciprocates thereon by means of a pivotable second handle. Cutting edges on the distal end of the crossbar bite against the footplate to cut away a small portion of tissue with each reciprocation of the crossbar. After use, the rongeur should be subject to a sterilization cycle before being reused. However, only the distal end of the rongeur, in the region of the footplate, typically comes into contact with tissue. Thus, there is a need in the art for a rongeur that has detachable tips that are easy to use. There is also a need for a rongeur that has detachable tips that can be one use only or disposable product. There is also a need for a rongeur with a detachable tip so that there is reduced chance of the footplate breaking, the cutting edges always remain sharp, and there is less fatigue to the surgeons using the product.

SUMMARY OF THE INVENTION

A rongeur in accordance with the present invention meets these needs by having an elongated shank having a distal end and a proximal end. A bore is disposed in the distal end of the shank. An elongated crossbar has a distal end and a proximal end adapted to reciprocate axially with respect to the shank. The crossbar moves between a retracted position and a tissue capturing position position. A bore is disposed in the distal end of the crossbar. A first handle is fixedly connected to the shank proximal end. A second handle is pivotably attached to the shank proximal end about a pivot axis. A first tip is selectively connected to the shank. The first tip has a proximal end and a distal end. The proximal end has a reduced diameter post. In the selectively connected position the reduced diameter post of the first tip is received in the bore of the shank. A second tip is selectively connected to the crossbar. The second tip has a proximal end and a distal end. The proximal end has a reduced diameter post. In the selectively connected position the reduced diameter post of the second tip is received in the bore of the shank.

BRIEF DESCRIPTION OF THE DRAWINGS

FIG. 1 is an exploded perspective view of a rongeur according to the present invention;
FIG. 2A is a front elevation view of the rongeur of FIG. 1 in the forward or tissue capturing position;
FIG. 2B is a front elevation view of the rongeur of FIG. 1 in the relaxed or crossbar retracted position;
FIG. 3 is a top view of the rongeur of FIG. 1;
FIG. 4 is a front elevation view of the rongeur of FIG. 1 with parts broken away;
FIG. 5 is a cross sectional view taken along lines 5-5 of FIG. 4;
FIG. 6 is a cross sectional view taken along lines 6-6 of FIG. 4;
FIG. 7 is cross sectional view taken along lines 7-7 of FIG. 6;
FIG. 8 is a cross sectional view taken along lines 8-8 of FIG. 4;
FIG. 9 is an enlarged view of the detachable tips; and
FIG. 10 is a cross sectional view taken along lines 10-10 of FIG. 9.

DETAILED DESCRIPTION

FIG. 1 illustrates a rongeur 10 according to the present invention. Rongeur 10 comprises an elongated shank 12 having a distal end 14 and proximal end 16. A crossbar 20 slideably engages the shank 12 and also comprises a distal end 22 and proximal end 24. A bore 23 is disposed in the distal end 22 of shank 12 for selectively receiving a detachable tip 34. Similarly, a bore 25 is disposed in the distal end 22 of crossbar 20 for selectively receiving a detachable tip 36. A first handle 26 extends downwardly from the shank proximal end 16 in fixed relation to shank 12. A second handle 28 pivotably attaches to the shank 12 near its proximal end 16 and pivots about an axis 30. A spring 32 between the first and second handles 26 and 28 biases them apart to the relaxed or crossbar retracted position as shown in FIG. 2B. A pair of detachable tips 34, 36 are shown in an exploded view in FIG. 1. Lower or first tip 34 extends from shank 12. Upper or second tip 36 extends from crossbar 20. Tips 34, 36 are detachably connected to shank 12 and crossbar 20, respectively. A footplate 18 extends upwardly from tip 34 at its distal end. When the user moves handles 26, 28 toward each other, overcoming the spring bias of spring 32, crossbar 20 and tip 36 slide toward the footplate 18 until the distal end of tip 36 engages with footplate 18 so that the rongeur is in the forward or tissue capturing position as shown in FIG. 2A, which will be described in further detail below.

As further seen in FIGS. 4, 6 and 7, a T-shaped spline 38 depends downwardly form a lower surface 40 of the crossbar 20. A mating inverse T-shaped slot 42 is formed in shank 12. Slot 42 narrows from a wider portion 44 to a narrower portion 46. The ends 38a, 38b of T-shaped spline 38 are sufficiently sized to prevent T-shaped spline 38 from being withdrawn from the narrow portion 44 of slot 42, but to permit removal from the wider portion 44. Crossbar 20 can thus be brought into sliding contact with shank 12 by inserting T-shaped spline 38 through the wider portion of slot 42. Crossbar 20 can then be slid toward the distal end of the shank 12 so that the T-shaped spline 38 is under the narrow portion 46 of slot 42 as illustrated in FIG. 6 to thereby allow slideable axial movement between the crossbar 20 and shank 12 without allowing the crossbar 20 to lift off of the shank 12. It will be appreciated by one of skill in the art that the locations of the splines and slots can be reversed and that other engaging shapes can be substituted therefor.

Turning further to FIGS. 2A, 2B, 3, 4, 8A, 8B, 9 and 10 tips 34, 36 and their detachment mechanism with shank 12 and crossbar 20 are illustrated. A spring biased release lever 48 is pivotably connected to shank 12. Similarly, a spring biased release lever 50 is pivotably connected to crossbar 20. Release levers 48 and 50 work in the same manner and, thus, release lever 48 will be described in detail. For the sake of brevity in this detailed description only the details of release lever 48 will be describe. One skilled in the art will readily recognize how to make and use release lever 50 based on the description of release lever 48. Referring to FIG. 3, a recess 52 is formed in both crossbar 20 and shank 12 to permit movement or depression of the release levers 48, 50 about their respective pivot points 54. A spring 56 biases the release levers 48, 50 into the engaged or locked position shown in FIG. 8A. To disengage or unlock the release levers 48, 50, the user can push the release levers 48, 50 into the respective shank 12 and crossbar 20 in the direction indicated by arrow A in FIG. 8B at location 58 on the release lever. This action can be done simultaneously, when the handles are in the relaxed position of FIG. 2B, if desired by the user. As shown in FIG. 2B, the release levers are aligned when handles 26, 28 are in the relaxed or crossbar retracted position. By pushing on lever 48 in the direction indicated by arrow A, lever 48 pivots about pin 54. Lever 48 has a pair of projecting shoulders 60, 62. Tip 34 has a mating pair of recessed slots 64, 66. When lever 48 is depressed to the position shown in FIG. 2B, the user can grab the tips 34, 36 and pull them away from the shank 12 and crossbar 20, in the direction indicated by arrow B in FIG. 8B, to remove them from rongeur 10. The tips can now be disposed of and a new set of tips 34, 36 can be used. Thus, there is a reduced chance of the footplate breaking, the cutting edges always remain sharp since they are used only during one procedure, and there is less fatigue to the surgeons using the product. While currently not preferred, the tips can be subject to a sterilization process and reused. However, to readily identify if the tips have been subject to a sterilization cycle, the tips have a sterilization mark or indicator 100 disposed therein, as shown in FIG. 9, which will change color should the tips be subject to a sterilization cycle. Tips 34, 36 are selectively slidingly connected to each other in a manner similar to how shank 12 and crossbar are selectively connected together. As further seen in FIGS. 1, 9 and 10, a T-shaped spline 68 depends downwardly form a lower surface 70 of tip 36. A mating inverse T-shaped slot 72 is formed in shank 12. Slot 72 narrows from a wider portion 74 to a narrower portion 76. The ends 68a, 68b of T-shaped spline 68 are sufficiently sized to prevent T-shaped spline 68 from being withdrawn from the narrow portion 74 of slot 72, but to permit removal from the wider portion 74. Tip 36 can thus be brought into sliding contact with tip 34 by inserting T-shaped spline 68 through the wider portion of slot 72. Tip 36 can then be slid toward the distal end of tip 34 and footplate 18 so that the T-shaped spline 68 is under the narrow portion 76 of slot 72 as illustrated in FIG. 9 to thereby allow slideable axial movement between the tip 36 and tip 34 without allowing the tip 36 to lift off of tip 34. It will be appreciated by one of skill in the art that the locations of the splines and slots can be reversed and that other engaging shapes can be substituted therefor. To insert a new set of tips 34, 36 into the shank 12 and crossbar 20, the tips 34, 36 are preferably placed in their slideable connected position as shown in FIG. 9. The user can then grab the tips 34, 36 and insert them, in the direction opposite to arrow B in FIG. 8B, into the shank 12 and crossbar 20. Each tip 34, 36 has at its proximal end reduced diameter post 78, 80, in which recesses 64, 66 are disposed. The proximal end of each tip has a beveled surface 82, 84 to facilitate insertion of the tips into the respective shank and crossbar. The distal end of each lever 48, 50 has a mating beveled surface 86 to facilitate insertion of the tips into the respective shank and crossbar. Thus, when the user initially inserts the reduced diameter posts 78, 80 of each tip 34, 36 into the respective shank and crossbar, lever 48, 50 will move to the position shown in FIG. 8B. The user can continue to insert the tips 34, 36 into the respective shank and crossbar until fully inserted at which time levers 48, 50 will snap into the position shown in FIG. 8A and lock the tip 34 with shank 12 and tip 36 with crossbar 20 as shown, for example, in FIGS. 2A, 2B and 4.

A pin 88 on the crossbar 20 rides within a slot 90 on an upper portion 92 of the second handle 28 so that when the second handle 28 is squeezed toward the first handle 26 by an operator the slot 90 moves distally and the action of the pin 88 therein drives the crossbar 20 distally. Second handle 28 pivots about pin 94, which is fixedly connected to first handle 26 and shank 12. Turning further to FIG. 4, the footplate 18 comprises an anvil cutting surface 96 about a tissue receiving recess 98 and a stress relieving groove between the footplate 18 and tip 34 as more fully described in U.S. Pat. No. 4,990,148 to Worrick, III et al., which is hereby fully incorporated herein by reference. Cutting edges on the distal end of tip 36 engage the anvil surface 96 whereby tissue, as for instance bone, trapped therebetween is cut.

The invention now being fully described, it will be apparent to one of ordinary skill in the art that many modifications and changes can be made thereto without departing from the spirit or scope of the invention as defined in the following claims.

What is claimed is:

1. A rongeur comprising:
   an elongated shank having a distal end and a proximal end, a bore being disposed in the distal end of the shank;
   an elongated crossbar having a distal end and a proximal end adapted to reciprocate axially with respect to the shank, the crossbar moving between a retracted position and a tissue capturing position, a bore being disposed in the distal end of the crossbar;
   a first handle fixedly configured to the shank proximal end and a second handle pivotably attached to the shank proximal end about a pivot axis;
   a first tip selectively connected to the shank, the first tip having a proximal end and a distal end, the proximal end having a reduced diameter post with a pair of recessed slots disposed therein, wherein in a selectively connected position the reduced diameter post of the first tip is received in the bore of the shank;
   a second tip selectively connected to the crossbar, the second tip having a proximal end and a distal end, the proximal end having a reduced diameter post with a pair of recessed slots disposed therein, wherein in a selectively connected position the reduced diameter post of the second tip is received in the bore of the crossbar; and
   a first release lever connected to the shank and a second release lever connected to the crossbar, each of the first and second release levers having a pair of projecting shoulders, wherein the pair of recessed slots in each of the first and second tips matingly receives the pair of projecting shoulders on the first and second release levers, respectively.

2. A rongeur according to claim 1, wherein the first release lever is pivotably connected to the shank.

3. A rongeur according to claim 2, wherein the second release lever is pivotably connected to the crossbar.

4. A rongeur according to claim 3 further comprising a first spring disposed between the shank and the first release lever that biases the first release lever into a first tip locked position.

5. A rongeur according to claim 4 further comprising a second spring disposed between the crossbar and the second release lever that biases the second release lever into a second tip locked position.

6. A rongeur according to claim 5 wherein a first recess is disposed in the shank to permit pivotable movement of the first release lever.

7. A rongeur according to claim 6 wherein a second recess is disposed in the crossbar to permit pivotable movement of the second release lever.

8. A rongeur according to claim 1, wherein a slot in the pair of recessed slots within each of the first and second tips has at least one angularly oriented edge, wherein the at least one angularly oriented edge is less than 90° relative to a bottom surface of the slot.

9. A rongeur according to claim 1, wherein an entirety of slots in the pair of recessed slots within each of the first and second tips has at least one angularly oriented edge, wherein the at least one angularly oriented edge is less than 90° relative to a bottom surface of the slot.

10. A rongeur according to claim 1, wherein a slot in the pair of recessed slots within each of the first and second tips has one angularly oriented edge and one perpendicularly oriented edge, wherein the angularly oriented edge is less than 90° relative to a bottom surface of the slot and wherein the perpendicularly oriented edge is 90° related to the bottom surface of the slot.

11. A rongeur according to claim 1, wherein at least one shoulder in the pair of projecting shoulders within each of the first and second release levers has at least one angularly oriented edge, wherein the at least one angularly oriented edge is less than 90° relative to a top surface of the at least one shoulder.

12. A rongeur according to claim 1, wherein a distal end of each of the first and second release levers further comprises a mating beveled surface.

13. A rongeur according to claim 7, wherein each of the first and second springs is positioned at least partially within each of the first and second recesses, respectively.

14. A rongeur according to claim 7, wherein each of the first and second release levers further comprises a push area aligned each of the first and second recesses, respectively, wherein the push area of each of the first and second release levers is positioned directly over the first and second spring, respectively.

15. A rongeur according to claim 1, further comprising a sterilization indicator positioned each of the first and second tips.

* * * * *